United States Patent
Takai

(10) Patent No.: US 6,733,676 B2
(45) Date of Patent: May 11, 2004

(54) DIALYZING SYSTEM AND METHOD OF OPERATING THE SAME

(75) Inventor: Ichiro Takai, Nagoya (JP)

(73) Assignees: Nipro Corporation, Osaka-fu (JP); Nikkiso Co., Ltd., Tokyo-to (JP); Nextier Co., Ltd., Shizuoka-ken (JP)

( * ) Notice: Subject to any disclaimer, the term of this patent is extended or adjusted under 35 U.S.C. 154(b) by 72 days.

(21) Appl. No.: 10/076,488

(22) Filed: Feb. 19, 2002

(65) Prior Publication Data

US 2002/0113016 A1 Aug. 22, 2002

(30) Foreign Application Priority Data

Feb. 19, 2001 (JP) ........................ 2001-041504
Nov. 20, 2001 (JP) ........................ 2001-354236

(51) Int. Cl.⁷ .................. B01D 61/22; B01D 61/14; B01D 61/32; B01D 61/28
(52) U.S. Cl. .................. 210/650; 210/85; 210/90; 210/97; 210/138; 210/143; 210/321.65; 210/646; 210/739; 210/741
(58) Field of Search ................ 210/85, 90, 97, 210/138, 143, 321.65, 645, 646, 650, 739, 741

(56) References Cited

U.S. PATENT DOCUMENTS

| | | | |
|---|---|---|---|
| 4,021,341 A | * 5/1977 | Cosentino et al. | ............ 210/87 |
| 4,680,122 A | * 7/1987 | Barone | ........................ 210/637 |
| 4,762,618 A | * 8/1988 | Gummesson et al. | ....... 210/637 |
| 5,211,849 A | 5/1993 | Kitaevich et al. | ........... 210/645 |
| 5,487,827 A | * 1/1996 | Peterson et al. | .............. 210/87 |
| 5,580,460 A | * 12/1996 | Polaschegg | ................. 210/646 |
| 6,077,443 A | * 6/2000 | Goldau | ........................ 210/741 |

FOREIGN PATENT DOCUMENTS

| | | |
|---|---|---|
| DE | 197 34 002 C1 | 9/1998 |
| DE | 198 21 534 C1 | 8/1999 |
| EP | 0 604 753 A2 | 7/1994 |
| EP | 0 911 044 A1 | 4/1999 |

* cited by examiner

Primary Examiner—John Kim
(74) Attorney, Agent, or Firm—Birch, Stewart, Kolasch & Birch, LLP

(57) ABSTRACT

A dialyzing system comprises a dialyzer 10 and an ultrafiltration-regulating unit 24 for regulating inflow and out flow of a dialysate to or from the dialyzer 10 to regulate ultrafiltration. The dialyzing system is adapted to determine a blood pressure from a dialysate pressure detected by a pressure transducer 28 at the time of temporary suspension of the ultrafiltration without use of a special line for measurement of pressure in the blood flow line and free from danger of blood leakage from the blood flow line.

14 Claims, 1 Drawing Sheet

DIALYZING SYSTEM AND METHOD OF OPERATING THE SAME

FIELD OF THE INVENTION

The present invention relates to a dialyzing system and an operating method thereof. More particularly, the present invention relates to an improved dialyzing system of the kind wherein waste products are removed and ultrafiltration is performed from the blood by allowing the blood to come into contact with a dialysate across semi-permeable membranes, and to a method for advantageously operating such a dialyzing system.

BACKGROUND OF THE INVENTION

Recently, various kinds of blood purification have been developed and put into practical use to perform treatment of end-stage renal failure patients by purifying the blood drawn from the patient's body and returning the purified blood to the patients' body. For this end, there have been widely used a dialyzing system, which generally comprises a dialyzer adapted to allow a blood and a dialysate, which flow into the dialyzer and flow out from the same through a blood flow line and a dialysate flow line, respectively, to be brought into contact with each other across semi-permeable membranes (i.e., dialysis membranes) such as hollow fiber membranes of cellulose, cuprammonium rayon, polysulfone, polyacrylonitrile or the like; and an ultrafiltration unit for regulating inflow and outflow rates of the dialysate entering into and discharging from the dialyzer through the dialysate flow lines.

In such a dialyzing system, the blood fed into the dialyzer is brought into contact with the dialysate fed into the dialyzer across the semi-permeable membrane in the dialyzer, thereby performing removal of waste products from the blood under the action of diffusion due to concentration gradients between the blood and the dialysate. On the other hand, excess water is removed from the blood through the semi-permeable membrane by ultrafiltration developing due to increase in the outflow rate of the dialysate from the dialyzer compared to the inflow rate of the dialysate to the dialyzer. The ultrafiltration unit regulates the inflow and outflow rates of the dialysate to and from the dialyzer.

In general, when purifying the patient's blood with a dialyzing system, it is essential for safe extracorporeal circulation of the patient's blood to take all sorts of expeditious measures in response to fluctuation in a pressure of the blood returning the patient's body. For this end, such a dialyzing system is generally adapted to monitor such fluctuation in pressure in the blood flow line through a pressure-detecting line. This pressure-detecting line is connected at one end to an air chamber arranged in the blood flow line downstream of the dialyzer and at the other end to a pressure transducer. Moreover, an air filter is arranged in the pressure-detecting line. Thus, the pressure in the blood flow line downstream of the dialyzer is directly detected through the pressure-detecting line.

The above conventional dialyzing system, however, has serious problems such that an inner wall of the pressure-detecting line, the pressure transducer and/or air filter are polluted with the blood flowing into the pressure-detecting line whenever air leakage takes place at the connecting portion of the pressure-detecting line and the pressure transducer due to loosening of engagement. Since it is general practice to use the pressure transducer and the air filter repeatedly and since perfect cleaning, sterilization or disinfection of these members is difficult because of their complex structures, patients treated with such dialyzing system are exposed to high risks for various infectious diseases.

Therefore, before operating a conventional dialyzing system, it is needed to carefully inspect the pollution of the pressure transducer and the air filter arranged in the pressure-detecting line. If any pollution is found in these members, sufficient disinfectious treatment must be immediately made, and such treatment makes the operation of dialyzing system troublesome.

SUMMARY OF THE INVENTION

It is therefore an object of the present invention to provide an improved dialyzing system, which makes it possible to monitor the fluctuation of a pressure in the blood flow line in a convincing way which is free from the blood flow line.

Another object of the present invention is to provide a method of advantageously operating such a dialyzing system.

The present invention is based on the following two findings; the pressure of the blood in the central part of the dialyzer is equal to the pressure of the dialysate when dialysis is performed without any ultrafiltration, and a pressure in the specified site of the blood flow line, such as the air-blood chamber arranged in the blood flow line downstream of the dialyzer, is related to the pressure of the blood in the central part of the dialyzer. This makes it possible to determine a pressure of the blood in the specified site of the blood flow line from the pressure of dialysate detected when the ultrafiltration is stopped during dialysis.

According to the present invention, these objects are achieved by providing a dialyzing system comprising:
a dialyzer;
an ultrafiltration unit with which ultrafiltration is performed from the blood through semi-permeable membranes in the dialyzer by regulating an outflow rate of a dialysate from the dialyzer to become greater than an inflow rate of the dialysate to the dialyzer; and
a pressure-detecting means arranged in a dialysate flow line to detect a pressure of the dialysate;
wherein said system is adapted to determine a pressure in a blood flow line on the basis of the pressure of the dialysate detected by the pressure-detecting means at the time of temporary stop of ultrafiltration due to temporary stop of the operation of the ultrafiltration unit.

Since the dialyzing system of the present invention has need not to provide a pressure-detecting line for detecting the pressure in the blood flow line. Thus, there is no chance of leakage of the blood from the blood flow line associated with the leakage at the connecting portion of the pressure-detecting line and the pressure transducer, which would often occur when the pressure in the blood flow line is directly measured through the pressure-detecting line. As a result, inspecting steps for the pollution of the apparatus by blood prior to the operation of the dialyzing system become unnecessary, and the time and labor spent for such inspection can be eliminated.

In a preferred embodiment of the dialyzing system according to the present invention, the pressure in the blood flow line is determined by a control system on the basis of the dialysate pressure continuously detected during ultrafiltration and a difference between the dialysate pressure detected at the time of temporary stop of the ultrafiltration and the dialysate pressure just stabilized after the subsequent resumption of the ultrafiltration.

The difference between the dialysate pressure detected when ultrafiltration is temporarily stopped and the dialysate pressure just stabilized after subsequent resumption of the ultrafiltration is substantially equal to the difference between the blood pressure and the dialysate pressure measured when ultrafiltration is developing (i.e., transmembrane pressure). Therefore, in the present invention, the blood pressure in the dialyzer when ultrafiltration is developing is continuously monitored by adding the difference between the dialysate pressure detected when ultrafiltration is temporarily stopped and the dialysate pressure detected when a steady state is just reached after resumption of ultrafiltration to the dialysate pressure at any given time during ultrafiltration.

In a preferred embodiment of the present invention, such temporary stop of ultrafiltration is done at certain time intervals and/or whenever the ultrafiltration rate is changed.

Thereafter, the dialysate pressure is measured at the point in time the dialysate pressure is just stabilized after the resumption of ultrafiltration, so as to calculate the difference between the dialysate pressure detected at the time of temporary stop of ultrafiltration and the dialysate pressure thus-measured just stabilized after the resumption of the ultrafiltration. Thus, even after the ultrafiltration rate is optionally changed, a correct pressure of the blood in the dialyzer can be continuously monitored and/or displayed.

The dialyzing system further may include monitoring means and/or display means which directly or indirectly monitors and/or displays the pressure in the blood flow line determined by the control system. The provision of such monitoring or displaying means contributes to improve usability of the dialyzing system advantageously, which in turn ensures safer purification of the blood.

Preferably, the dialyzing system is adapted to monitor and/or display a pressure of blood at a specified site of the blood flow line. Such pressure of the blood at a specified site of the flow line is determined on the basis of the detected pressure of the dialysate and a pressure gradient from the central part of the dialyzer to the specified site, which is calculated from a flow resistance of the blood flow line and the blood flow rate.

Therefore, the dialyzing system of the present invention can be advantageously operated while reliably monitoring the pressure at an optional site in the blood flow line without any risk for leakage of blood from the blood flow line or any problem caused thereby, such as the pollution of the dialyzing system due to contact with the leaked blood, or any increase in the number of steps of disinfection and inspection of the dialyzing system in terms of pollution by the leaked blood. As a result, the extracorpreal circulation of the patient's blood and the purification thereof can be efficiently carried out in more safety.

According to the present invention, the dialyzing system is operated by a method including the steps of:

temporarily stopping the operation of the ultrafiltration unit to equalize a dialysate inflow rate into a dialyzer and a dialysate outflow rate from the dialyzer;

detecting a pressure of the dialysate, which is equal to the pressure in the blood flow line in the central part of the dialyzer, during every temporary stop of ultrafiltration; and monitoring a fluctuation in the pressure of the dialysate as a fluctuation of a pressure of the blood.

The present invention will become more fully understood from the detailed description given hereinbelow and the accompanying drawings, which are given by way of illustration only. However, it should be understood that the detailed description and specific example, while indicating preferred embodiments of a dialyzing system of the invention, are given by way of illustration only, since various changes and modifications within the spirit and scope of the invention will become apparent to those skilled in the art from the detailed description.

DETAILED DESCRIPTION OF THE INVENTION

Figure 1:
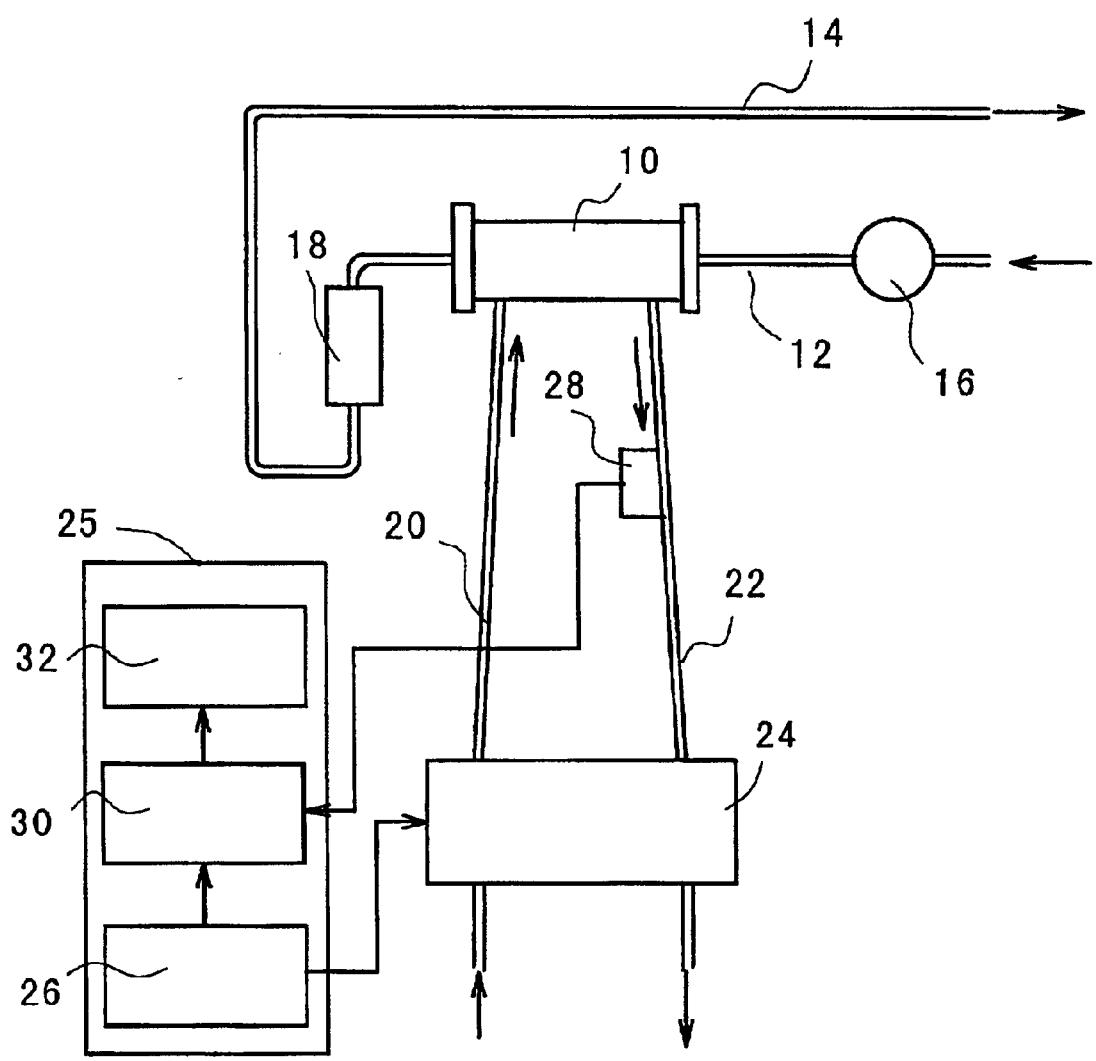
FIG. 1 is a schematic diagram of an embodiment of the dialyzing system of the present invention.

Referring now to FIG. 1, there is shown a schematic diagram illustrating an embodiment of a dialyzing system according to the present invention. In FIG. 1, reference numeral 10 denotes a dialyzer or purifier of a known structure used for blood purification, which comprises, for example, a cylindrical casing and semi-permeable hollow fiber membranes held therein.

The dialyzer 10 is connected at one end thereof to a blood flow line 12 for introducing the blood from a patient's body, and connected at the opposite end thereof to a blood flow line 14 for returning the purified blood into the patient's body. In other words, the blood flow line is composed of the blood inflow line 12 for introducing the blood from the patient's body, the blood flow site in the dialyzer 10, and the blood outflow line 14 for returning the purified blood into the patient's body. The blood inflow line 12 is provided with a blood pump 16 to allow the blood to pass through the blood inflow line 12, the dialyzer 10 and the blood outflow line 14. On the other hand, the blood outflow line 14 is provided with an air-blood chamber 18 for removing the air involved in the blood from the blood passing through the blood inflow line 12, the dialyzer 10 and the blood outflow line 14.

Further, the dialyzer 10 is connected to a dialysate inflow line 20 for introducing a fresh dialysate from a tank (not illustrated in the drawing) into the dialyzer 10, and a dialysate outflow line 22 for discharging the waste dialysate from the dialyzer 10. Thus, the dialysate flow line in this embodiment is composed of the dialysate inflow line 20, the dialysate flow site in the dialyzer 10 and the dialysate outflow line 22.

The dialyzing system further includes a ultrafiltration-regulating unit 24 of a known construction for regulating ultrafiltration rate and for regulating dialysate supply and discharge rates to and from the dialyzer 10. The ultrafiltration-regulating unit 24 is arranged in the dialysate inflow line 20 and the dialysate outflow line 22 to supply a fresh dialysate from the tank to the dialyzer 10 through the dialysate inflow line 20 as well as to discharge the waste dialysate from the dialyzer 10 through the dialysate outflow line 22. The waste dialysate contains waste products and excessive water removed from the blood by diffusion and filtration through the semi-permeable membranes in the dialyzer 10.

The above ultrafiltration-regulating unit 24 is controlled by a control system 25 including a control unit 26, a monitoring unit 30 and a display unit 32. The control unit 26 regulates the inflow and outflow rates of the dialysate passing through the dialyzer 10.

When the ultrafiltration-regulating unit 24 receives ultrafiltration-start signals sent from the control unit 26, it increases the outflow rate of the waste dialysate from the dialyzer 10 than the inflow rate of the fresh dialysate to the dialyzer, whereby allowing the dialyzer 10 to develop ultrafiltration from the blood as well as to regulate the ultrafiltration rate on the basis of a difference between the outflow rate of the waste dialysate and the inflow rate of the fresh dialysate. On the other hand, when the ultrafiltration-regulating unit 24 receives signals for the stop of ultrafiltration from the control unit 26, it regulates the outflow rate of the waste dialysate so as to become equal to the inflow rate of the fresh dialysate, thereby stopping the ultrafiltration to make the ultrafiltration rate zero. As will understood from the above description, the ultrafiltration system in the above embodiment is constituted by the ultrafiltration-regulating unit 24 and the control system 25. The control system 25 includes control unit 26, which controls the activity of the ultrafiltration-regulating unit 24 including the temporary stop of ultrafiltration.

In this embodiment, the control unit 26, which outputs the ultrafiltration-start signal and the ultrafiltration-stop signal to the ultrafiltration-regulating unit 24, includes a timer unit of a known type. By clock signal of the timer unit, the control unit 26 gives the ultrafiltration-start signal and the ultrafiltration-stop signal alternately to the ultrafiltration-regulating unit 24. For example, the dialyzing system is adapted to stop the ultrafiltration for just 30 seconds at every 5-minute interval.

The dialyzing system further includes a pressure transducer 28 of a known type, which is arranged in the dialysate outflow line 22 or the dialysate inflow line 20 and serves as a pressure-detecting means. The pressure transducer detects the pressure of the dialysate in the dialysate outflow line 22 or the dialysate inflow line 20. It is known that the pressure of the dialysate in the dialysate outflow line 22 or the dialysate inflow line 20 is correlated with the pressure of the dialysate in the central part of the dialyzer 10. With the dialyzing system of the present invention, therefore, the pressure of the dialysate in the central part of the dialyzer is calculated from the pressure of the dialysate in the dialysate outflow line 22 or the dialysate inflow line 20.

Further, the dialysate pressure in the central part of the dialyzer 10 is equal to the blood pressure in the central part of the dialyzer 10 when ultrafiltration is not performed. Therefore, the dialysate pressure detected by the transducer 28 is adapted to be continuously monitored by a monitoring unit 30 with a computing function, which converts the detected pressure to a value corresponding to a pressure at a specified site of the blood outflow line and displays the result on a display unit 32.

Specifically, the dialysate pressure in the dialysate outflow line 22 or the dialysate inflow line 20, which has a correlation with the dialysate pressure in the central part of the dialyzer 10, is detected by the pressure transducer 28 and input to the monitoring unit 30. On the other hand, the control signals (i.e., the ultrafiltration-start signal or the ultrafiltration-stop signal), which are output from the control unit 26, are input not only to the ultrafiltration-regulating unit 24 but also to the monitoring unit 30. By receiving the ultrafiltration-stop signal from the control unit 26, the monitoring unit 30 detects a point in time when the inflow rate of the dialysate to the dialyzer 10 is made equal to the outflow rate of the dialysate from the dialyzer 10 (i.e., the point when the pressure difference between the dialysate pressure and the blood pressure is eliminated in the dialyzer 10). At this point in time, the monitoring unit 30 decides on the basis of the detected signals sent from the pressure transducer 28 that the dialysate pressure at the central part of the dialyzer is substantially equal to the blood pressure at the central part of the dialyzer 10. Thus, the monitoring unit 30 converts the detected dialysate pressure to a blood pressure in the dialyzer, which is monitored and displayed on the display unit 32.

Also, by receiving the ultrafiltration-start signal from the control unit 26, the monitoring unit 30 is adapted to decide that the ultrafiltration-regulating unit 24 resumes the ultrafiltration. Then, by monitoring the signal from the pressure transducer 28, the monitoring unit 30 determines the pressure of the dialysate at the point in time when the signal input from the pressure transducer 28 reaches stabilized level after ultrafiltration is resumed. This value of the dialysate pressure during ultrafiltration is compared with the value of the dialysate pressure measured just before the temporary stop of the ultrafiltration, so as to calculate the difference between them. On the basis of the resultant difference, the monitoring unit 30 calculates the blood pressure in the central part of the dialyzer 10 when the dialysate pressure in the dialysate outflow line 22 is just stabilized after ultrafiltration is resumed. Even after the pressure in the dialysate outflow line 22 has been stabilized, the dialysate pressure in the central part of the dialyzer 10 is continuously determined so as to calculate the blood pressure continuously. The thus-calculated values of the blood pressure is continuously monitored by the monitoring unit 30 and displayed on the display unit 32 to monitor fluctuations in the blood pressure with time.

When the control unit 26 receives a signal to change the ultrafiltration rate from a ultrafiltration rate-setting device (not illustrated in the drawing), it outputs a signal for stopping the ultrafiltration before changing the ultrafiltration rate, in order to determine the dialysate pressure at the time when ultrafiltration is not performed. Then, the control unit 26 allows the ultrafiltration-regulating unit 24 to resume ultrafiltration at the new rate. Once the signals monitored by the pressure transducer 28 is stabilized after ultrafiltration is resumed, the dialysate pressure at this point in time is stored as the standard value of the dialysate pressure during ultrafiltration, and the difference is calculated between the dialysate pressure measured when ultrafiltration is stopped and the above-mentioned standard pressure during ultrafiltration as the difference between the pressure of the blood and the pressure of the dialysate in the central part of the dialyzer 10 (i.e., transmembrane pressure). The thus calculated transmembrane pressure is then used to determine the blood pressure in the central part of the dialyzer 10 from the dialysate pressure at any given point in the during ultrafiltration phase.

Preferably, the predetermined blood flow resistance value of the blood flow line is stored in the calculating unit of the monitoring unit 30. In such case, it is possible to determine, by the calculation, not only the blood pressure in the central part of the dialyzer 10 but also the blood pressure at any position in the blood outflow line, for example, at a position of the air-blood chamber 18 arranged in the blood outflow line 14. Thus, the dialyzing system of the present invention enables easier and more safe measurement of the blood pressure at an optional site in the blood flow line, which in turn provides more excellent usability.

The display unit 32 includes a display unit of a known type (not illustrated) and displays the blood pressure transmitted from the monitoring unit 30. The fluctuation in the blood pressure with the time can be visually observed on the screen of the display unit 32.

When carrying out the dialysis, the dialyzing system of the above structure is operated in the following manner.

First, the blood pump 16 in the blood flow line 12 is continuously actuated to perform continuous extracorporeal circulation of the patient's blood. At the same time, the timer unit included in the control unit 26 is operated. Then, the ultrafiltration rate is first set to zero by adjusting the inflow rate of the dialysate to the dialyzer 10 to the rate equal to the outflow rate of the dialysate from the dialyzer 10. During such zero-ultrafiltration phase, removal of the waste product from the blood flowing into the dialyzer 10 and replenishment of constituents required for the blood from the fresh dialysate to the blood are performed by diffusion of respective constituents according to their concentration gradients between the blood and the dialysate.

Then, the monitoring unit 30 detects a blood pressure, which is equal to the dialysate pressure when ultrafiltration rate is zero, on the basis of the dialysate pressure detected by the pressure transducer 28. After the dialysate pressure is detected by the pressure transducer and monitored by the monitoring unit 30 during the zero-ultrafiltration phase, an outflow rate of the dialysate from the dialyzer is increased to a value greater than the inflow rate of the fresh dialysate into the dialyzer 10 by the ultrafiltration-regulating unit 24. As a result, ultrafiltration is started in response to the difference between the inflow of the fresh dialysate flowing into the dialyzer 10 and the outflow rate of the dialysate flowing out from the dialyzer 10. After the dialysate pressure detected during ultrafiltration phase by transducer 28 is stabilized, the calculating unit of the monitoring unit 30 calculates a difference between the dialysate pressure detected during zero-ultrafiltration phase and post stabilization dialysate pressure during subsequent-ultrafiltration phase, which is substantially equal to the difference between the pressure of the blood and that of the dialysate when ultrafiltration is developing (i.e., transmembrane pressure). Then, the calculating unit of the monitoring unit 30 determines the blood pressure in the dialyzer 10 on the basis of the thus-obtained difference in the dialysate pressure between the zero-ultrafiltration phase and the subsequent ultrafiltration phase (i.e., transmembrane pressure). Further, the calculating unit of the monitoring unit 30 may continuously calculate the blood pressure at an optional point in the blood outflow line 14 including a position of the air-blood chamber, taking into account of the flow resistance of the blood flow line and the blood flow rate.

The determined value of the blood pressure is sent in the form of electric signals from the monitoring unit 30 to the display unit 32 and displayed on the monitor screen. By monitoring the blood pressure displayed on the monitor screen, it is possible for an operator to know fluctuation in blood pressure with time. If an abnormal pressure change is observed, the medical practitioner investigates the causes for such a change and takes adequate action therefor quickly.

If the timer unit of the control unit 26 indicates the time to stop ultrafiltration by checking the predetermined time schedule in terms of operation of the ultrafiltration-regulating unit 24, or if the ultrafiltration rate is changed during dialysis, the control unit 26 immediately outputs the ultrafiltration-stop signal and then determines the blood pressure in the dialyzer 10, which is equal to the dialysate pressure measured by the pressure transducer 28. After that, the control unit 26 sends a signal for ultrafiltration resumption to the ultrafiltration-regulating unit 16. When the pressure signal from the pressure transducer 28 is stabilized, the calculation unit of the monitoring unit 30 calculates the difference between the dialysate pressure detected during the zero-ultrafiltration phase and the just-stabilized dialysate pressure during the subsequent ultrafiltration phase. Then, the calculation unit calculates the blood pressure based on the above pressure difference between the two phases (the zero-ultrafiltration phase and the ultrafiltration phase) and the dialysate pressure is monitored continuously after the dialysate pressure is stabilized during the ultrafiltration phase. The thus-calculated pressure on the blood side is monitored and displayed on the display unit 32. Thus, the operator monitors and checks an abnormal change in the pressure on the blood side, observing the display. If an abnormal change is found, the operator investigates the causes for such a change and makes an adequate operation.

As described above, according to the above embodiment, the pressure on the side of the blood is always displayed on the monitor screen of the control unit 26 while a patient is on dialysis, and therefore, fluctuation in the pressure on the side of the blood can be monitored at real time. Accordingly, the causes for an abnormal fluctuation can be immediately investigated and a treatment for such a fluctuation can be rapidly made. Thus, the hemodialysis treatment can be carried out more safely.

In addition, according to the above embodiment, the pressure on the side of the blood can be calculated from the pressure of the dialysate which is detected by the pressure transducer 28 arranged in the dialysate outflow line 22 or the dialysate inflow line 20. Therefore, in the dialyzing system of the present invention, there is no need to provide a pressure measuring line from the blood outflow line, which is indispensable to the conventional dialyzing system. Accordingly, those dangers including pollution caused by the leakage of the blood in association with the troubles in the pressure measuring line are utterly eliminated in the dialyzing system of the present invention.

The construction of the present invention which has been described above in detail is given as an illustrative example only, to which the scope of the present invention is not limited in any way.

For example, while the dialyzer 10 according to the above embodiment is composed of the cylindrical casing which holds the semi-permeable membrane of hollow fibers therein, the structure of the dialyzer is not limited to this in any way, and any of the known various structures of dialyzer included in conventional dialyzing systems can be employed.

In the above embodiment, regarding the pressure on the side of the blood which is calculated and monitored by the monitoring unit 30, the calculation factors to be inputted to the calculation unit can be any value and any equation, in so far as they are theoretically correct. For example, an equation for the difference in pressure of blood between the central part of the dialyzer 10 and a specified site of the blood outflow line 14 can be added to the calculation factors. It is apparent that by the equation, the blood pressure difference between the central part of dialyzer 10 and the specified site of the blood outflow line 14 can be calculated from the known blood flow rate and the flow resistance of the blood flow line, which is determined on the basis of the specific of the dialyzer 10, the length of the blood flow line from the dialyzer 10 and the specified site of the blood outflow line 14. The pressure in the specified site of the blood outflow line 14 is calculated on the basis of the above difference between the central part of dialyzer 10 and the specified site of the blood outflow line 14. It is also possible to display the thus-calculated value of the pressure in the specified site of the blood outflow line 14 on the monitor screen.

While the display unit 32 according to the above embodiment includes the monitor in which the screen displays a value of the pressure from the monitoring unit 30, the above embodiment may dispense with such display unit 32, and a simple display lamp or an alarm informing that a value of the pressure has reached the predetermined value, may be used instead of the display unit 32.

Further, the means for detecting the pressure of the dialysate is not limited to that of the above embodiment, and any of known devices having a structure detectable of the pressure of dialysate may be appropriately used instead of the means described in the above embodiment.

In the above embodiment, the ultrafiltration unit is composed of the ultrafiltration-regulating unit 24, which regulates the inflow rate of the dialysate to the dialyzer 10 and the outflow rate of the dialysate from the dialyzer 10 under the control by the control unit 26. However, the structure of such ultrafiltration unit is not particularly limited, and any of known structures may be optionally employed, in so far as the ultrafiltration can be made from the blood through the semi-permeable membrane in the dialyzer 10 by making the outflow rate of the dialysate from the dialyzer 10 to be greater than the inflow rate of the dialysate to the dialyzer 10.

For example, the ultrafiltration unit may be provided by composing the ultrafiltration-regulating unit 24 so that the inflow rate of the dialysate to the dialyzer 10 and the outflow rate of the dialysate from the dialyzer 10 is always kept constant, and separately providing an ultrafiltration pump which pulls out the dialysate from the dialysate outflow line 22 connected to the dialyzer 10, so as to perform ultrafiltration from the blood through the semi-permeable membrane in the dialyzer 10.

In the above embodiment, the control of stop and resumption of ultrafiltration is performed automatically based on the counting by the timer unit included in the control unit 26 or on the basis of the timing for change of the setting of the ultrafiltration rate. However, such control may be manually made, using a simple switch or the like, thereby stopping or resuming the ultrafiltration.

Even where the periodic stop and resumption of the ultrafiltration by the ultrafiltration-regulating unit 24 is automatically controlled based on the counting by the timer unit included in the control unit 24, the time interval between the stop and the resumption of the ultrafiltration is not limited to that described in the above embodiment, and such interval may be appropriately determined according to other factors of a whole of the treatment by dialysis.

Further, in the above embodiment, the control unit 26 includes the timer unit, and the monitoring unit 30 includes the calculating unit. However, such timer unit and such calculating unit may be included in any of the units of the dialyzing system, in so far as sufficient functions can be performed in order to control a whole of the dialyzing system. For example, such units can be included in the control unit 26, the monitoring unit 30, the body portion of the display unit 32, and the like. Otherwise, such units can be included in units which are electrically or mechanically connected to the dialyzing system. However, the scope of the present invention is not limited by such a structure in any way.

In the above embodiment, fluctuation in the pressure of the dialysate detected when ultrafiltration is stopped and performed is monitored as the fluctuation in the pressure on the side of the blood in the dialyzer and/or in an optional site in blood flow line. Whereas, for example, it is also possible to monitor only the fluctuation in the dialysate detected at every time when the ultrafiltration is stopped, as the fluctuation in the pressure on the side of the blood.

Although specified exemplification is saved, it is possible to carry out the present invention in various modes including alteration, modification, improvement, etc. based on the knowledge of those skilled in the art, and such modes are of course included in the scope of the present invention, in so far as they do not go beyond the gist of the present invention.

As will be understood from the foregoing description, the dialyzing system of the present invention makes it possible to reliably monitor the fluctuation in the pressure in the blood flow line, and to thereby purify the blood in more safety. In addition, it also becomes possible to eliminate the chance of leakage of the blood from the blood flow line, which would be caused by troubles of the unit for monitoring the fluctuation in the pressure. Therefore, advantageously, the portions with pollution due to the direct contact with the blood can be eliminated, and the labor and time spent for inspecting such pollution prior to the operation can be very effectively reduced.

Further, according to the method of operating the dialyzing system of the present invention, becomes possible to operate the dialyzing system in very safety and in advantageous manners while reliably monitoring the fluctuation in the pressure in the blood flow line, without any leakage of the blood from the blood flow line and any trouble caused by such leakage of the blood.

What is claimed is:

1. A dialyzing system comprising:
   a dialyzer having a dialysate outflow line and a dialysate inflow line;
   an ultrafiltration unit connected to the dialyzer by the dialysate outflow line and the dialysate inflow line for regulating a rate of an ultrafiltration process by regulating an outflow rate of a dialysate from the dialyzer so as to become greater than an inflow rate of the dialysate to the dialyzer;
   pressure-detecting means arranged in one of the dialysate flow lines to detect a pressure of the dialysate; and
   control means for calculating the pressure of a blood flow line connected to the dialyzer based on the pressure of the dialysate detected by the pressure-detecting means and for calculating a pressure gradient in the blood flow line based on a blood flow rate and a flow resistance of the blood flow line,
   said control means being adapted to determine the pressure of a blood flow line based on the pressure of the dialysate detected by the pressure-detecting means at a time of a temporary stop of the ultrafiltration process caused by temporarily stopping an operation of the ultrafiltration unit,
   wherein the control means monitors and displays the pressure of the blood flow line as a pressure of a specified site of the blood flow line.

2. The dialyzing system according to claim 1, wherein the control means determines the pressure of the blood flow line based on the pressure of the dialysate continuously detected by the pressure-detecting means during the ultrafiltration process and a difference between the pressure of the dialysate at the time of the temporary stop of the ultrafiltration process and a newly stabilized dialysate pressure during in ultrafiltration process at a time of stable ultrafiltration, said stabilized pressure of the dialysate being determined by detection of the pressure of the dialysate after a lapse of a certain time period required for stabilization of the pressure of the dialysate during the ultrafiltration process from a time at which the ultrafiltration process is resumed.

3. The dialyzing system according to claim 1, wherein the control means determines the pressure of the blood flow line predetermined time intervals or at a time when the ultrafiltration rate is changed.

4. The dialyzing system according to claim 1, wherein the control means further comprises monitoring means and display means which directly or indirectly monitor and display the determined pressure of the blood flow line.

5. A method for operating a dialyzing system, comprising the steps of:
   temporarily stopping an ultrafiltration operation of an ultrafiltration unit to equalize an inflow of a dialysate into a dialyzer and an outflow of the dialysate from the dialyzer;
   detecting the pressure of the dialysate at every temporary stop of the ultrafiltration operation;
   calculating the pressure of a blood flow line connected to the dialyzer from the detected pressure of the dialysate;
   calculating a pressure gradient in the blood flow line based on a blood flow rate and a flow resistance of the blood flow line; and
   monitoring and displaying the pressure of the blood flow line as a pressure of a specified site of the blood flow line.

6. The method for operating a dialyzing system according to claim 5, further comprising the steps of:
   determining the pressure of the blood flow line by continuously detecting the pressure of the dialysate during the ultrafiltration operation and a difference between the pressure of the dialysate at the time of a temporary stop of the ultrafiltration operation and a newly stabilized dialysate pressure during the ultrafiltration operation at a time of stable ultrafiltration; and
   determining said stabilized pressure of the dialysate by detecting the pressure of the dialysate after a lapse of a certain time period required for stabilizing the pressure of the dialysate during the ultrafiltration operation from a time at which the ultrafiltration operation is resumed.

7. The method of operating a dialyzing system according to claim 5, further comprising the step of:
   determining the pressure of the blood flow line at predetermined time intervals or at a time when a rate of an ultrafiltration operation is changed.

8. A dialyzing system comprising:
   a dialyzer having a dialysate outflow line and a dialysate inflow line;
   an ultrafiltration unit connected to the dialyzer by the dialysate outflow line and the dialysate inflow line for regulating a rate of an ultrafiltration process by regulating an outflow rate of a dialysate from the dialyzer to a rate greater than an inflow rate of the dialysate to the dialyzer;
   pressure-detecting means arranged in one of the dialysate flow lines to detect a pressure of the dialysate; and
   control means for regulating and controlling said ultrafiltration unit to temporarily stop or resume the ultrafiltration process and for determining a pressure of a blood flow line connected to the dialyzer on the basis of the pressure of the dialysate detected by the pressure-detecting means, said control means comprising:
      timer means for alternately generating signals to temporarily stop and to resume the a ultrafiltration process;
      calculating means for determining a pressure of a blood flow line based on the pressure of the dialysate detected by said pressure-detecting means at a time of a temporary stop of the ultrafiltration process caused by the temporary ultrafiltration-stop signal from the timer means; and
      means for monitoring and displaying the determined pressure of the blood flow line.

9. The dialyzing system according to claim 8, wherein the control means determines the pressure of the blood flow line, based on the pressure of the dialysate continuously detected by said pressure-detecting means during a ultrafiltration process and a difference between the pressure of the dialysate at the time of the temporary stop of the ultrafiltration process and a newly stabilize dialysate pressure during ultrafiltration at a time of stable ultrafiltration process, said stabilized dialysate pressure being determined by detection of the dialysate pressure after a lapse of a certain time period required for stabilization of the ultrafiltration process from a time at which the water removal is resumed.

10. The dialyzing system according to claim 8, wherein said calculating means determine the pressure of the blood flow line at predetermined time intervals or at time when the ultrafiltration rate is changed.

11. The dialyzing system according to claim 8, wherein the control means further comprises monitoring means and display means which directly or indirectly monitor and display the determined pressure of the blood flow line.

12. The dialyzing system according to claim 8, wherein the calculating means calculate the pressure of the blood flow line based on the detected pressure of the dialysate and a pressure gradient in the blood flow line, said pressure gradient being determined based on a blood flow rate and a flow resistance of the blood flow line, and wherein the control means monitors and display the calculated pressure of the blood flow line as a pressure of a specified site of a blood flow line.

13. The dialyzing system according to claim 8, wherein said control means allows aid ultrafiltration unit to regulate the outflow rate of the dialysate to a rate equal to the inflow rate of the dialysate to temporarily stop the ultrafiltration when it receives said temporary stop signal sent from said timer means, but allows said ultrafiltration unit to increase the outflow rate of the dialysate from the dialyzer to a rate greater than the inflow rate of a fresh dialysate to the dialyzer to develop ultrafiltration in the dialyzer when it receives a signal for resumption of ultrafiltration sent from said timer means.

14. The dialyzing system according to claim 8, wherein the control system further includes a ultrafiltration rate-setting device for setting an ultrafiltration rate, and wherein said control means, when received a signal sent from said ultrafiltration rate-setting device, outputs a signal for temporary stop of ultrafiltration before changing the ultrafiltration rate to determine the dialysate pressure just before the stop of ultrafiltration.

* * * * *